United States Patent
Utku (10) Patent No.: US 8,642,512 B2
(45) Date of Patent: Feb. 4, 2014

(54) METHOD OF DETECTING EARLY IMMUNE ACTIVATION

(75) Inventor: Nalân Utku, Dortmund (DE)

(73) Assignee: Cellact Pharma GmbH, Dortmund (DE)

( * ) Notice: Subject to any disclaimer, the term of this patent is extended or adjusted under 35 U.S.C. 154(b) by 1170 days.

(21) Appl. No.: 11/914,617

(22) PCT Filed: May 17, 2006

(86) PCT No.: PCT/EP2006/004689
§ 371 (c)(1),
(2), (4) Date: Jul. 14, 2008

(87) PCT Pub. No.: WO2006/122791
PCT Pub. Date: Nov. 23, 2006

(65) Prior Publication Data
US 2008/0274910 A1    Nov. 6, 2008

(30) Foreign Application Priority Data
May 17, 2005 (EP) .................................. 05010683

(51) Int. Cl.
*C07K 16/00* (2006.01)
(52) U.S. Cl.
USPC ..................... 506/9; 506/13; 506/17; 506/23
(58) Field of Classification Search
None
See application file for complete search history.

(56) References Cited

FOREIGN PATENT DOCUMENTS

| WO | WO 99/11782 | * | 3/1999 | .............. C12N 15/12 |
|----|-------------|---|--------|---------------------------|
| WO | WO 03/054018 | * | 7/2003 | .............. C07K 16/00 |
| WO | WO 03/093318 | * | 11/2003 | .............. C07K 16/28 |
| WO | WO 2004/042346 | | 5/2004 | |

OTHER PUBLICATIONS

Tamura et al., Mar. 2005, TIRC7 Pathway as a traget for preventing allograft rejection, Drug News Perspect. 18(2): 103-108.*
van Venrooij et al., Autoimmunity Reviews, 6: 37-41, 2006.*
Avouac et al., Ann. Rheum. Dis., 65: 845-851, 2006.*
Jordan et al., Pediatr. Nephrol., 25: 2035-2048, 2010.*
Kumamoto et al., Transplant Immunology, 16: 238-244, 2006.*
Shulzhenko et al., 2001, Monitoring of Intragraft and Peripheral Blood TIRC7 Expression as a Diagnostic Tool for Acute Cardiac Rejection in Humans, Human Immunology, 62: 342-347.*
Natalia Shulzhenko et al.: Monitoring of intragraft and peripheral blood TIRC7 expression as a diagnostic tool for acute cardiac rejection in humans, in: HUMAN IMMUNOLOGY, vol. 62, No. 4, Apr. 2001, pp. 342-347.
Tamura et al.: TIRC7 pathway as a target for preventing allograft rejection, in: DRUG NEWS AND PERSPECTIVES 2005 SPAIN, vol. 18, No. 2, Mar. 2005.
Non-invasive monitoring of TIRC7 mRNA in urine is predictive for acute rejection after human kidney alltransplantation:, in: TRANSPLANTATION, vol. 82, No. 1 Suppl. 2, Jul. 15, 2006, p. 641.

* cited by examiner

*Primary Examiner* — Cecilia J Tsang
*Assistant Examiner* — Li Lee
(74) *Attorney, Agent, or Firm* — Saliwanchik, Lloyd & Eisenschenk (57) ABSTRACT

Provided are methods of diagnosing an early immune activation by detecting T-cell immune response cDNA 7 (TIRC7); in particular, TIRC7 as an early biomarker for the detection of transplant rejection in a non-invasive diagnostic methods is described that replaces biopsy intervention with a simple diagnostic method for monitoring after transplantation and furthermore, kits for uses in such methods of diagnosis are provided.

10 Claims, 1 Drawing Sheet

| Test | Sensitivity* | Specificity** |
|---|---|---|
| CT > 0,01 | 100% | 50% |
| CT > 0,03 | 90% | 80% |
| CT > 0,05 | 70% | 100% |

METHOD OF DETECTING EARLY IMMUNE ACTIVATION

BACKGROUND OF THE INVENTION

The present invention relates to diagnostic methods of detecting early immune activation by detecting the T-cell immune response cDNA 7 (TIRC7). In particular, the present invention provides TIRC7 as an early biomarker for the detection of transplant rejection in a noninvasive diagnostic method that replaces biopsy interventions with a simple diagnostic method for monitoring after transplantation. Furthermore, the present invention relates to kits for use in such methods of diagnosis.

T-cell activation is a serial process involving multiple signaling pathways and sequential changes in gene expression resulting in differentiation of T-cells into distinct subpopulations, i.e. Th1 and Th2, which are distinguishable by their pattern of cytokine production and characterize the mode of cellular immune response. The T-cell response is initiated by the interaction of the antigen-specific T-cell receptor (TCR) with a peptide presented by major histocompatibility complex (MHC) molecules on the surface of antigen presenting cells (APCs). Additional signals are provided by a network of receptor-ligand interactions mediated by a number of membrane proteins such as CD28/CTLA4 and B7, CD40/CD40L, LFA-I and ICAM-1 (Lenschow, Science 257 (1992), 789-792; Linsley, Annu. Rev. Immunol. 11 (1993), 191-212; Xu, Immunity 1 (1994), 423-431; Bachmann, Immunity 7 (1997), 549-557; Schwartz, Cell 71 (1992), 1065-1068) collectively called costimulatory signals (Perez, Immunity 6 (1997), 411-417). These membrane proteins can alter T-cell activation in distinct ways (Bachmann, Immunity 7 (1997), 549-557) and regulate the immune response by the integration of positive and negative signals provided by these molecules (Bluestone, Immunity 2 (1995), 555-559; Perez, Immunity 6 (1997), 411-417). Many of the agents which are effective in modulating the cellular immune response either interfere with the T-cell receptor (Cosimi, Transplantation 32 (1981), 535-539) block costimulatory signaling (Larsen, Nature 381 (1996), 434-438; Blazar J. Immuno. 157 (1996), 3250-3259; Kirk, Proc. Natl. Acad. Sci. USA 94 (1997), 8789-8794; Linsley, Science 257 (1992), 792-95; Turka, Proc. Natl. Acad. Sci. USA 89 (1992), 11102-11105) or inhibit intracellular activation signals downstream from these primary cell membrane triggers (Schreiber and Crabtree, Immunology Today 13 (1992), 136-42). Therapeutic prevention of T-cell activation in organ transplantation and autoimmune diseases presently relies on pan-immunosuppressive drugs interfering with downstream intracellular events. Specific modulation and detection of the immune response, e.g., in transplantation therapy remains a longstanding goal in immunological research.

For example, acute rejection (aRx) has a major impact on the long-term outcome of renal allografts, and its diagnosis is contingent on the invasive procedure of allograft biopsy. New immunosuppressive protocols have reduced the incidence but have not abolished this problem. Moreover, aRx is now more frequently seen several weeks after transplantation in outpatients. A non-invasive diagnostic test for predicting aRx could improve the management and outcome.

Hence, there is a the need of early biomarker and non-invasive diagnostic methods to detect activation of the immune response, in particular for conditions where activation of the immune response is related to a disease or disorder, for example transplant rejection.

SUMMARY OF THE INVENTION

The solution to this technical problem is achieved by providing the embodiments characterized in the claims, and described further below.

Accordingly, the present invention relates to a preferably non-invasive method of diagnosing an early and/or undesired immune response, said method comprising analyzing expression T-cell immune response cDNA 7 (TIRC7) in a sample.

The term "TIRC7", also known as T-cell immune regulator 1 (TCIRGI), as used in accordance with the present invention, denotes a protein involved in the signal transduction of T-cell activation and/or proliferation and that, preferably in a soluble form is capable of inhib-king inhibiting or suppressing T-cell proliferation in response to alloactivation in a mixed lymphocyte culture or in response to mitogens when exogenously added to the culture. In vitro translated TIRC7 protein is able to efficiently suppress in a dose dependent manner the proliferation of T-cells in response to alloactivation in a mixed lymphocyte culture or in response to mitogens. TIRC7 is known to the person skilled in the art and described, inter alia, in WO99/11782; Utku et al., Immunity 9 (1998), 509-518 and Heinemann et al., Genomics 57 (1999), 398-406. The nucleotide and amino acid sequence are also described in international application WO99/11782 and Heinemann et al. (1999), supra. Hence, the present inventors have described a novel cell surface molecule on T and B cells (Utku et al., J. Immunol. 173 (2004), 2342-2352). Antibody targeting of TIRC7 utilizing various animal models showed significant prevention of organ rejection of kidney or heart allografts via induction of CTLA4 and reduction of CD25 expression on T cells (Utku et al., Immunity 9 (1998), 509-518; Kumamoto et al., Am. J. Transplant 4 (2004), 505-154).

In accordance with the present invention, it could be established that T-cell immune response cDNA 7 (TIRC7) TIRC7 is expressed upon immune activation early in peripheral blood lymphocytes and remains induced in inflammatory cells before and during rejection after kidney transplantation as well as in joints from patients with established rheumatoid arthritis. Moreover, it was surprisingly found that TIRC7 expression in bodily fluids such as urine corresponds to histological examination of TIRC7 expression; see Examples 1 and 2. Hence, the measurement of urinary TIRC7 mRNA expression offers a new non-invasive approach for determining the status of the immune system.

Using the Taqman PCR approach to analyze the expression of TIRC7 in urine of patients 2 days prior to organ rejection after kidney transplantation led to the discovery of the beneficial and advantageous use of TIRC7 as an early biomarker to detect the immune activation at a earlier stage without using an invasive method such as biopsy. In context with disorders and diseases which are caused by or attacked by an immune response of the human body this allows for example to either increase or decrease the immune therapeutic dose of the respective treatment to optimize treatment of patients, for example transplant recipients.

In this respect, it is readily understood that the method of the present invention can also be used for monitoring the activity of immune suppressing agents, wherein the down-regulation of the expression of TIRC7 compared to non-treated subject is indicative of a suppressed or non-activated immune response. Put in other words, the present invention also relates to the methods described herein for determining a suppressed immune response.

In principle, the method of the present invention can be applied to any condition where it is desired to evaluate the status of an immune response, if any. Usually, said immune response is evoked by an infectious or inflammatory disease. Preferably, said inflammatory disease is an autoimmune disease, for example psoriasis, multiple sclerosis, arthritis, or transplant rejection. In a particular preferred embodiment of the method of the present invention, said disease is kidney transplant rejection or rheumatoid arthritis.

From the test sample is obtained a genetic sample. The genetic sample comprises a nucleic acid, preferably RNA. For example, in determining the expression of TIRC7 one can obtain mRNA from the test sample, and the mRNA may be reverse transcribed into cDNA for further analysis. In another embodiment, the mRNA itself is used in determining the expression of TIRC7. In some embodiments, the expressions level of TIRC7 may be determined by determining the level/presence of a gene product (e.g., protein) thereby eliminating the need to obtain a genetic sample from the test sample. Polyclonal and monoclonal antibodies against TIRC7 as well as nucleic acid probes are described in, e.g., WO99/11782 and Utku et al, Immunity 9 (1998), 509-518; see also supra.

Preferably there is enough of the test sample to obtain a large enough genetic sample to accurately and reliably determine the expression levels of TIRC7. In certain embodiments, multiple samples may be taken in order to obtain a representative sampling.

A genetic sample, e.g. nucleic acid sample may be obtained from the test sample using any techniques known in the art (Ausubel et al. Current Protocols in Molecular Biology (John Wiley & Sons, Inc., New York, 1999); Molecular Cloning: A Laboratory Manual, 2nd Ed., ed. by Sambrook, Fritsch, and Maniatis (Cold Spring Harbor Laboratory Press: 1989); Nucleic Acid Hybridization (B. D. Hames & S. J. Higgins eds. 1984); the treatise, Methods in Enzymology (Academic Press, Inc., N.Y.); each of which is incorporated herein by reference). The nucleic acid may be purified from whole cells using DNA or RNA purification techniques. The genetic sample may also be amplified using PCR or in vivo techniques requiring subcloning. In a preferred embodiment, the genetic sample is obtained by isolating mRNA from the cells of the test sample and reverse transcribing the RNA into DNA in order to create cDNA (Khan et al., Biochem. Biophys. Acta 1423 (1999), 17-28; incorporated herein by reference).

Once a test sample has been obtained, it can be analyzed for the presence or absence of TIRC7. The analysis may be performed using any techniques known in the art including, but not limited to, sequencing, PCR, RT-PCR, quantitative PCR, restriction fragment length polymorphism, hybridization techniques, Northern blot, microarray technology, DNA microarray technology, etc. In determining the expression level of TIRC7 in a test sample, the level of expression may be normalized by comparison to the expression of another gene such as a well known, well characterized gene or a housekeeping gene; see also the Examples.

The expression data from TIRC7 may be analyzed using statistical methods described below in the Examples in order to determine the phenotype or characteristic of a particular immune response. The analyzed data may also be used to select/profile patients for a particular treatment protocol.

Analyzing expression in the methods of the present invention includes any qualitative or quantitative method for detecting expression of TIRC7, many of which are known in the art. The method can include analyzing expression of TIRC7 by measuring expression of TIRC7 using a quantitative method, or by using a qualitative method. Non-limiting methods for analyzing polynucleotides and polypeptides are discussed below. Preferably, expression is analyzed using methods that are directed to polynucleotides.

Hence, in a preferred embodiment of the method of the present invention the sample comprises a nucleic acid, wherein expression of TIRC7 is analyzed by detecting polynucleotides encoding TIRC7, and wherein an increase in expression of TIRC7 is indicative of the activation of the immune response. The method of the present invention may comprise for example the step of extracting nucleic acid from a biological sample. The presence, i.e. amount or absence of the TIRC7 nucleic acid target gene is detected, if present. Preferably, the nucleic acid is amplified prior detection. A preferred method of amplification is by reverse transcription and polymerase chain reaction (PCR). In one embodiment of the invention the PCR further comprises nested PCR.

In preferred embodiments, the method may further comprise preparing at least two pairs of primers complementary to regions of TIRC7 nucleic acids.

The methods of analyzing the presence of TIRC7 can also utilize a biochip, or other miniature high-throughput technology. The manufacture and use of biochips such as those involving bioarrays, are known in the art and commercially available; see, e.g., bioarrays available from Sigma-Genosys (The Woodlands, Tex.); Affymetrix (Santa Clara, Calif.), and Full Moon Biosystems (Sunnyvale, Calif.). For reviews of Biochips and bioarrays see, e.g., Kallioniemi, Ann. Med. 33 (2001), 142-147; and Rudert, Curr. Opin. Mol. Ther. 2 (2000), 633-642).

Such bioarrays can be analyzed using blotting techniques similar to those discussed below for conventional techniques of detecting polynucleotides and polypeptides. Other microfluidic devices and methods for analyzing gene expression, especially those in which more than one gene can be analyzed simultaneously and those involving high-throughput technologies, can be used for the methods of the present invention.

Quantitative measurement of expression levels using bioarrays is also known in the art, and typically involve a modified version of a traditional method for measuring expression as described herein. For example, such quantitation can be performed by measuring a phosphor image of a radioactive-labeled probe binding to a spot of a microarray, using a phosphohor imager and imaging software. Analytical bioinformatic methods for analyzing bioarray data such as of nucleic acid microarray data are available and described in the prior art; see, e.g., international application WO03/067217.

The methods of the present invention typically employ RNA, including messenger RNA (mRNA), isolated from a skin sample. The RNA may be single stranded or double stranded. Enzymes and conditions optimal for reverse transcribing the template to DNA well known in the art can be used. Alternatively, the RNA can be subjected to RNAse protection assays. A DNA-RNA hybrid that contains one strand of each can also be used. A mixture of polynucleotides can also be employed, or the polynucleotides produced in a previous amplification reaction, using the same or different primers may be so used. In the instance where the polynucleotide sequence is to be amplified the polynucleotide sequence may be a fraction of TIRC7, or can be present initially as a discrete molecule, such that the specific sequence is the entire nucleic acid. It is not necessary that the sequence to be amplified be present initially in a pure form; it may be a minor fraction of a complex mixture.

In addition, RNAse protection assays can be used if RNA is the polynucleotide obtained from the sample. In this procedure, a labeled antisense RNA probe is hybridized to the complementary polynucleotide in the sample. The remaining unhybridized single-stranded probe is degraded by ribonuclease treatment.

The hybridized, double stranded probe is protected from RNAse digestion. After an appropriate time, the products of the digestion reaction are collected and analyzed on a gel (see for example Ausubel et al., CURRENT PROTOCOLS IN MOLECULAR BIOLOGY, section 4.7. 1 (1987)). As used herein, "RNA probe" refers to a ribonucleotide capable of hybridizing to RNA in a sample of interest. Those skilled in the art will be able to identify and modify the RNAse protection assay specific to the polynucleotide to be measured, for example, probe specificity may be altered, hybridization temperatures, quantity of nucleic acid etc. Additionally, a number of commercial kits are available, for example, RiboQuant™ Multi-Probe RNAse Protection Assay System (Pharmingen, Inc., San Diego, Calif.).

In another embodiment, the polynucleotide in the sample may be analyzed by a blotting procedure, typically a Northern blot procedure. For blotting procedures polynucleotides are separated on a gel and then probed with a complementary polynucleotide to the sequence of interest. For example, RNA is separated on a gel transferred to nitrocellulose and probed with complementary DNA to one of the melanoma differentially-diagnosed genes disclosed herein. The complementary probe may be labeled radioactively, chemically etc. Hybridization of the probe is indicative of the presence of the melanoma of interest.

The detection of polynucleotides may optionally be performed by using radioactively labeled probes. Any radioactive label may be employed which provides an adequate signal. Other labels include ligands, colored dyes, and fluorescent molecules, which can serve as a specific binding pair member for a labeled ligand, and the like. The labeled preparations are used to probe for a polynucleotide by the Southern or Northern hybridization techniques, for example. Nucleotides obtained from samples are transferred to filters that bind polynucleotides. After exposure to the labeled polynucleotide probe, which will hybridize to nucleotide fragments containing target nucleic acid sequences, the binding of the radioactive probe to target nucleic acid fragments is identified by autoradiography (see Genetic Engineering, 1 ed. Robert Williamson, Academic Press (1981), pp. 72-81). The particular hybridization technique is not essential to the invention. Hybridization techniques are well known or easily ascertained by one of ordinary skill in the art. As improvements are made in hybridization techniques, they can readily be applied in the method of the invention.

Probes according to the present invention and used in a method of the present invention selectively hybridize to TIRC7 are disclosed herein. In preferred embodiments, the probes are spotted on a bioarray using methods known in the art. As used herein, the term "selective hybridization" or "selectively hybridize", refers to hybridization under moderately stringent or highly stringent conditions such that a nucleotide sequence preferentially associates with a selected nucleotide sequence over unrelated nucleotide sequences to a large enough extent to be useful in detecting expression of TIRC7. It will be recognized that some amount of nonspecific hybridization is unavoidable, but is acceptable provided that hybridization to a target nucleotide sequence is sufficiently selective such that it can be distinguished over the non-specific cross-hybridization, for example, at least about 2-fold more selective, generally at least about 3-fold more selective, usually at least about 5-fold more selective, and particularly at least about 10-fold more selective, as determined, for example, by an amount of labeled oligonucleotide that binds to target nucleic acid molecule as compared to a nucleic acid molecule other than the target molecule, particularly a substantially similar (i.e., homologous) nucleic acid molecule other than the target nucleic acid molecule.

Conditions that allow for selective hybridization can be determined empirically, or can be estimated based, for example, on the relative GC:AT content of the hybridizing oligonucleotide and the sequence to which it is to hybridize, the length of the hybridizing oligonucleotide, and the number, if any, of mismatches between the oligonucleotide and sequence to which it is to hybridize (see, for example, Sambrook et al., "Molecular Cloning: A laboratory manual (Cold Spring Harbor Laboratory Press 1989)). An example of progressively higher stringency conditions is as follows: 2×SSC/O. 1% SDS at about room temperature (hybridization conditions); 0.2×SSC/O.1% SDS at about room temperature (low stringency conditions); 0.2×SSC/O.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

The polynucleotides encoding TIRC7 may be amplified before they are detected. The term "amplified" refers to the process of making multiple copies of the nucleic acid from a single polynucleotide molecule. The amplification of polynucleotides can be carried out in vitro by biochemical processes known to those of skill in the art. The amplification agent may be any compound or system that will function to accomplish the synthesis of primer extension products, including enzymes. Suitable enzymes for this purpose include, for example, E. coli DNA polymerase I, Taq polymerase, Klenow fragment of E. coli DNA polymerase I, T4 DNA polymerase, other available DNA polymerases, polymerase muteins, reverse transcriptase, ligase, and other enzymes, including heat-stable enzymes (i.e., those enzymes that perform primer extension after being subjected to temperatures sufficiently elevated to cause denaturation). Suitable enzymes will facilitate combination of the nucleotides in the proper manner to form the primer extension products that are complementary to each mutant nucleotide strand. Generally, the synthesis will be initiated at the 3'-end of each primer and proceed in the 5'-direction along the template strand, until synthesis terminates, producing molecules of different lengths. There may be amplification agents, however, that initiate synthesis at the 5'-end and proceed in the other direction, using the same process as described above. In any event, the method of the invention is not to be limited to the embodiments of amplification described herein.

One method of in vitro amplification, which can be used according to this invention, is the polymerase chain reaction (PCR) described for example in U.S. Pat. Nos. 4,683,202 and 4,683,195. The term "polymerase chain reaction" refers to a method for amplifying a DNA base sequence using a heat-stable DNA polymerase and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce rapid and highly specific amplification of the desired sequence. Many polymerase chain reaction methods are known to those of skill in the art and may be used in the method of the invention. For example, DNA can be subjected to 30 to 35 cycles of amplification in a thermocycler as follows: 95° C. for 30 sec, 52 to 60° C. for 1 min, and 72° C. for 1 min, with a final extension step of 72° C. for 5 min. For another example, DNA can be subjected to 35 polymerase chain reaction cycles in a thermocycler at a denaturing temperature of 95° C. for 30 sec, followed by varying annealing temperatures ranging from 54-58° C. for 1 min, an extension step at 70° C. for 1 min and a final extension step at 7O° C.

The primers for use in amplifying the polynucleotides of the invention may be prepared using any suitable method, such as conventional phosphotriester and phosphodiester methods or automated embodiments thereof so long as the primers are capable of hybridizing to the polynucleotides of interest. One method for synthesizing oligonucleotides on a modified solid support is described in U.S. Pat. No. 4,458,066. The exact length of primer will depend on many factors, including temperature, buffer, and nucleotide composition. The primer must prime the synthesis of extension products in the presence of the inducing agent for amplification.

Primers used according to the method of the invention are complementary to each strand of nucleotide sequence to be amplified. The term "complementary" means that the primers must hybridize with their respective strands under conditions, which allow the agent for polymerization to function, hi other words, the primers that are complementary to the flanking sequences hybridize with the flanking sequences and permit amplification of the nucleotide sequence. Preferably, the 3'-terminus of the primer that is extended has perfectly base paired complementarity with the complementary flanking strand.

Primers and probes for the differentially expressed TIRC7, can be developed using known methods combined with the present disclosure.

Those of ordinary skill in the art will know of various amplification methodologies that can also be utilized to increase the copy number of target nucleic acid. The polynucleotides detected in the method of the invention can be further evaluated, detected, cloned, sequenced, and the like, either in solution or after binding to a solid support, by any method usually applied to the detection of a specific nucleic acid sequence such as another polymerase chain reaction, oligomer restriction (Saiki et al., Bio/Technology 3 (1985), 1008-1012), allele-specific oligonucleotide (ASO) probe analysis (Conner et al., Proc. Natl. Acad. Sci. USA 80 (1983), 278), oligonucleotide ligation assays (OLAs) (Landegren et al., Science 241 (1988), 1077), RNAse Protection Assay and the like. Molecular techniques for DNA analysis have been reviewed (Landegren et al, Science 242 (1988), 229-237). Following DNA amplification, the reaction product may be detected by Southern blot analysis, without using radioactive probes. In such a process, for example, a small sample of DNA containing the polynucleotides obtained from the tissue or subject are amplified, and analyzed via a Southern blotting technique. The use of non-radioactive probes or labels is facilitated by the high level of the amplified signal. In one embodiment of the invention, one nucleoside triphosphate is radioactively labeled, thereby allowing direct visualization of the amplification product by autoradiography. In another embodiment, amplification primers are fluorescently labeled and run through an electrophoresis system. Visualization of amplified products is by laser detection followed by computer assisted graphic display, without a radioactive signal.

The methods of the present invention can involve a real-time quantitative PCR assay, such as a Taqman assay (Holland et al., Proc. Natl. Acad. Sci. USA, 88 (1991), 7276); see also Example 2. The assays can be performed on an instrument designed to perform such assays, for example those available from Applied Biosystems (Foster City, Calif.).

Primers and probes for such an assay can be designed according to known procedures in the art.

Simple visualization of a gel containing the separated products may be utilized to analyze TIRC7 according to the methods of the present invention. For example, staining of a gel to visualize separated polynucleotides, a number of stains are well known to those skilled in the art. However, other methods known to those skilled in the art may also be used, for example scanning densitometry, computer aided scanning and quantitation as well as others.

The method for detecting TIRC7 in accordance with the present invention may alternatively employ the detection of a polypeptide product of the TIRC7 gene. In this regard, the sample, as described herein, can be used as a source to isolate polypeptides. Measurement of a particular polypeptide can serve as a method of detecting, staging, diagnosing, monitoring, prognosing, or otherwise assisting in management of disorders related to the immune system. For example, following taking the sample, polypeptides may be quantified using methods known to those of skill in the art, for example by ELISA.

Monoclonal antibodies to a particular polypeptide can be used in immunoassays, such as in liquid phase or bound to a solid phase carrier, to detect TIRC7 polypeptide. In addition, the monoclonal antibodies in these immunoassays can be detectably labeled in various ways. Examples of types of immunoassays that can utilize monoclonal antibodies are competitive and non-competitive immunoassays in either a direct or indirect format. Examples of such immunoassays are the radioimmunoassay (RIA) and the sandwich (immunometric) assay. Detection of the polypeptide antigens using monoclonal antibodies can be done utilizing immunoassays, which are run in either the forward, reverse, or simultaneous modes, including immunohistochemical assays on physiological samples. Those of skill in the art will know, or can readily discern, other immunoassay formats without undue experimentation.

Preferably, antibodies recognizing the major (third) extracellular domain of TIRC7 (see FIG. 1 of WO99/11782) are used in the diagnostic methods of the present invention.

Particularly useful anti-TIRC7 antibodies are described in international applications WO03/054018 and WO03/054019.

The term "immunometric assay" or "sandwich immunoassay" includes simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

Monoclonal antibodies can be bound to many different carriers and used to detect the presence of TIRC7 polypeptide. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation. A TIRC7 polypeptide may be detected by the monoclonal antibodies when present in biological fluids.

In performing the assays it may be desirable to include certain "blockers" in the incubation medium (usually added with the labeled soluble antibody). The "blockers" are added to assure that non-specific proteins to anti-TIRC7 immunoglobulins present in the experimental sample do not crosslink or destroy the antibodies on the solid phase support, or the radiolabeled indicator antibody, to yield false positive or false negative results. The selection of "blockers" therefore may add substantially to the specificity of the assays.

It has been found that a number of nonrelevant (i.e., nonspecific) antibodies of the same class or subclass (isotype) as those used in the assays (e.g., IgGl, IgG2a, IgM, etc.) can be used as "blockers". The concentration of the "blockers" (normally 1-100 µg/ml) may be important, in order to maintain the proper sensitivity yet inhibit any unwanted interference by mutually occurring cross reactive proteins in the specimen.

As mentioned before, the sample is preferably a bodily fluid, e.g., urine, lymph, ascites, cerebral spinal fluid, synovial fluid, pleural effusion, sputum, stool, tears, sweat, pus, etc. Most preferably, said sample is urine; see also Example 2.

In another aspect, the present invention provides a non-invasive method for monitoring a suspicious immune response of a subject. The method includes analyzing expression of TIRC7 in a sample, preferably from urine at a first time point and a second time point, and comparing the expression at the first time point and the second time point.

Time points can include any interval of time, but are typically at least 2 weeks, and more typically at least 1 month apart. For certain embodiments, time points are 2 months, 3 months, 6 months, 1 year, or 2 years apart. Samples can be taken at any number of time points, including 2, 3, 4, 5, etc. time points. Comparison of expression analysis data from different time points can be performed using any of the known statistical methods for comparing data points to assess differences in the data, including time-based statistical methods such as control charting. TIRC7 can be identified in the time series, for example, by comparing expression levels to a cut-off value, or by comparing changes in expression levels to determine whether they exceed a cut-off change value, such as a percent change cut-off value.

The foregoing methods are preferably conducted at least twice on a given. Following detection, one may compare the results seen in a given patient with a statistically significant reference group of normal patients and tested patients. In this way, it is possible to correlate the determined expression level of TIRC7 with various clinical states or disease prognosis.

This embodiment is particularly useful for monitoring patients with a suppressed immune system because of for example transplantation purposes. Some people must take immunosuppressive drugs to prevent the rejection of a transplanted organ or because they have a disease in which the immune system attacks the body's own tissues (autoimmune illnesses); others may need radiation therapy to treat another form of cancer. Because of this, all people taking these immunosuppressive drugs or receiving radiation treatments should undergo TIRC7 expression examination at regular intervals. Therefore, the methods of the present invention are particularly advantageous for this patient group.

In a further embodiment, the method of the present invention is particularly useful for monitoring autoimmune diseases, in particular multiple sclerosis, during disease progression. Since the amount of TIRC7 protein appears to correlate with the state of the disease, detection of TIRC7 in patients undergoing medical treatment can be used for prognoses of the course of the healing process. Accordingly, the method of the present invention encompasses the detection of expression of TIRC7 in patients suffering from, for example, multiple sclerosis, vasculititis or tumors of the central nervous system (CNS) for diagnosing and more specifically monitoring the progression or degression of the disease. Most preferably, the bodily fluid to be used for taking a sample for analyzing the expression of TIRC7 is liquor or serum. Furthermore, the use of TIRC7 antibodies such as those described hereinbefore is preferred, in particular wherein these antibodies are labeled. However, the use of nucleic acid based techniques as described herein is also envisaged.

This embodiment is of course particularly suited for tailoring drug dosage and administration regimen in that dependent on the result of the method of the present invention either higher or lower concentrations of the drug are to be administered. For example, if a high amount of TIRC7 nucleic acid and protein, respectively, is detected a higher concentration of the drug may be administered and/or at shorter intervals. Thus, the methods of the present invention are particular advantageous in avoiding overdosing and underdosing a given drug.

In another embodiment the present invention provides a kit for use in a method of the present invention, comprising one or more nucleic acid or antibody probes or primers that selectively bind to TIRC7; and optionally comprising detection means.

Oligonucleotide primers can also be spotted on a bioarray which is provided in the kit. The kit can include a skin sample collection device and probes that selectively bind TIRC7. Such a kit may also include a carrier means being compartmentalized to receive in close confinement one or more containers such as vials, tubes, and the like, each of the containers comprising one of the separate elements to be used in the method. If present, a second container may comprise a lysis buffer. The kit can alternatively include a computer-type chip on which the lysis of the cell will be achieved by means of an electric current.

The kit can also have containers containing probes or primers for amplification of or hybridization to the target nucleic acid sequence which may or may not be labeled, or a container comprising a reporter, such as a biotin-binding protein, such as avidin or streptavidin, bound to a reporter molecule, such as an enzymatic, florescent, or radionuclide label. The term "detectably labeled deoxyribonucleotide" refers to a deoxyribonucleotides that is associated with a detectable label for detecting the deoxyribonucleotide. For example, the detectable label may be a radiolabeled nucleotide or a small molecule covalently bound to the nucleotide where the small molecule is recognized by a well-characterized large molecule. Examples of these small molecules are biotin, which is bound by avidin, and thyroxin, which is bound by anti-thyroxin antibody. Other methods of labeling are known to those of ordinary skill in the art, including enzymatic, fluorescent compounds, chemiluminescent compounds, phosphorescent compounds, and bioluminescent compounds.

The kit can include one or more primer pairs, including a forward primer that selectively binds upstream of the TIRC7 gene on one strand, and a reverse primer, that selectively binds upstream of the TIRC7 gene on a complementary strand.

As new markers are identified, different combinations may be developed that show optimal function with different ethnic groups or sex, different geographic distributions, different stages of disease, different degrees of specificity or different degrees of sensitivity. Marker combinations may also be developed, which are particularly sensitive to the effect of therapeutic regimens on disease progression. For example, enhanced granulysin mRNA expression in urinary sediment in early and delayed acute renal allograft rejection has been reported by Kotsch et al., in Transplantation 77 (2004), 1866-1875, the materials and methods of which described therein at pages 1867 and 1868 are specifically incorporated herein by reference.

Patients may be monitored after surgery, hypothermia, immunotherapy, cytokine therapy, gene therapy, radiotherapy or chemotherapy, to determine if a specific therapy is effective.

Hence, the present invention generally relates to the use of the methods disclosed herein for determining the risk and/or stage of a disease related to disorder or early activation of the immune response.

Further examples of disorders to be diagnosed in accordance with the method of the present invention include, but are not limited to, an immune system disorder such as inflammation, actinic keratosis, acquired immunodeficiency syndrome (AIDS), Addison's disease, adult respiratory distress syndrome, allergies, ankylosing spondylitis, amyloidosis, anemia, arteriosclerosis, asthma, atherosclerosis, autoimmune hemolytic anemia, autoimmune thyroiditis, bronchitis, bursitis, cholecystitis, cirrhosis, contact dermatitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, Graves' disease, Hashimoto's thyroiditis, paroxysmal nocturnal hemoglobinuria, hepatitis, hypereosinophilia, irritable bowel syndrome, episodic lymphopenia with lymphocytotoxins, mixed connective tissue disease (MCTD), multiple sclerosis, myasthenia gravis, myocardial or pericardial inflammation, myelofibrosis, osteoarthritis, osteoporosis, pancreatitis, polycythemia vera, polymyositis, psoriasis, Reiter's syndrome, rheumatoid arthritis, scleroderma, Sjgren's syndrome, systemic anaphylaxis, systemic lupus erythematosus, systemic sclerosis, primary thrombocythemia, thrombocytopenic purpura, ulcerative colitis, uveitis, Werner syndrome, complications of cancer, hemodialysis, and extracorporeal circulation, trauma, and hematopoietic cancer including lymphoma, leukemia, and myeloma; a reproductive disorder such as a disorder of prolactin production, infertility, including tubal disease, ovulatory defects, and endometriosis, a disruption of the estrous cycle, a disruption of the menstrual cycle, polycystic ovary syndrome, ovarian hyperstimulation syndrome, an endometrial or ovarian tumor, a uterine fibroid, autoimmune disorders, an ectopic pregnancy, and teratogenesis, cancer of the breast, fibrocystic breast disease, and galactorrhea, a disruption of spermatogenesis, abnormal sperm physiology, cancer of the testis, cancer of the prostate, benign prostatic hyperplasia, prostatitis, Peyronie's disease, impotence, carcinoma of the male breast, and gynecomastia; a nervous system disorder such as epilepsy, ischemic cerebrovascular disease, stroke, cerebral neoplasms, Alzheimer's disease, Pick's disease, Huntingdon's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, akathesia, amnesia, catatonia, diabetic neuropathy, tardive dyskinesia, dystonias, paranoid psychoses, postherpetic neuralgia, and Tourette's disorder; a cell signaling disorder including endocrine disorders such as disorders of the hypothalamus and pituitary resulting from lesions such as primary brain tumors, adenomas, infarction associated with pregnancy, hypophysectomy, aneurysms, vascular malformations, thrombosis, infections, immunological disorders, and complications due to head trauma; disorders associated with hyperpituitarism including acromegaly, giantism, and syndrome of inappropriate antidiuretic hormone (ADH) secretion (SIADH) often caused by benign adenoma; disorders associated with hypothyroidism including goiter, myxedema, acute thyroiditis associated with bacterial infection; disorders associated with hyperparathyroidism including Conn disease (chronic hypercalemia); pancreatic disorders such as Type I or Type II diabetes mellitus and associated complications; disorders associated with the adrenals such as hyperplasia, carcinoma, or adenoma of the adrenal cortex, hypertension associated with alkalosis; disorders associated with gonadal steroid hormones such as: in women, abnormal prolactin production, infertility, endometriosis, perturbations of the menstrual cycle, polycystic ovarian disease, hyperprolactinemia, isolated gonadotropin deficiency, amenorrhea, galactorrhea, hermaphroditism, hirsutism and virilization, breast cancer, and, in postmenopausal women, osteoporosis; and, in men, Leydig cell deficiency, male climacteric phase, and germinal cell aplasia, hypergonadal disorders associated with Leydig cell tumors, androgen resistance associated with absence of androgen receptors, syndrome of 5 a-reductase, and gynecomastia; and a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In a still further aspect the present invention relates to the use of a therapeutic agent, preferably immunosuppressive agent for the prevention or treatment of any one of the above-mentioned diseases of a subject, wherein said subject has been positively tested according to a diagnostic method of the present invention.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using Internet search engines. An overview of patent information in biotechnology and a survey of relevant sources of patent information useful for retrospective searching and for current awareness is given in Berks, TIBTECH 12 (1994), 352-364.

Several documents are cited throughout the text of this specification. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

The above disclosure generally describes the present invention. A more complete understanding can be obtained by reference to the following specific examples which are provided herein for purposes of illustration only and are not intended to limit the scope of the invention.

EXAMPLES

The examples which follow further illustrate the invention, but should not be construed to limit the scope of the invention in any way. Detailed descriptions of conventional methods, such as those employed herein can be found in the cited literature; see also "The Merck Manual of Diagnosis and Therapy" Seventeenth Ed. ed by Beers and Berkow (Merck & Co., Inc. 2003).

The practice of the present invention will employ, unless otherwise indicated, conventional techniques of cell biology, cell culture, molecular biology, transgenic biology, microbiology, recombinant DNA, and immunology, which are within the skill of the art. Methods in molecular genetics and genetic engineering are described generally in the current editions of Molecular Cloning: A Laboratory Manual, (Sambrook et al., (1989) Molecular Cloning: A Laboratory Manual, 2nd ed., Cold Spring Harbor Laboratory Press); DNA Cloning, Volumes I and II (Glover ed., 1985); Oligonucleotide Synthesis (Gait ed., 1984); Nucleic Acid Hybridization (Hames and Higgins eds. 1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, 3rd Edition (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu et al., eds.); Immobilized Cells And Enzymes (IRL Press, 1986); Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (Weir and Blackwell, eds., 1986). Reagents, cloning vectors, and kits for genetic manipulation referred to in this disclosure are available from commercial vendors such as BioRad, Stratagene, Invitrogen, and Clontech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251); Extracting information from cDNA arrays, Herzel et al., CHAOS 11, (2001), 98-107.

FIG. 1: TIRC7 as diagnostic marker in transplantation. Results of taqman per analysis using urine samples from kidney transplant patients (Average=0.131, Standard Deviation=0.115, n=10) compared with urine of transplanted patients with no rejection episode (Average=0.017, Standard Deviation=0.015, n=10). * Sensitivity: the probability that a test result is positive given the subject has the disease—estimated by: TP/(TP+FN)

** Specificity: the probability that a test result is negative given the subject does not have the disease—estimated by: TN/(TN+FP)

DETAILED DESCRIPTION OF PREFERRED EMBODIMENTS

The examples illustrate the invention.

Example 1

TIRC7 as diagnostic marker for early detection of immune activation.

The aim of this experiment was to examine the expression of TIRC7 in various tissues to analyze its potential role as biomarker to diagnose undesired immune response in an early phase. Therefore, the expression of the TIRC7 protein was surveyed using specific monclonal antibodies (mAbs) during rejection of human kidney allografts after transplantation, joint tissues and synovial fluid of established Rheumatoid Arthritis (RA) patients as well as in resting and activated Peripheral Blood Lymphocytes (PBL) of healthy volunteers.

Expression of TIRC7 was tested in clinical biopsies of renal allograft recipients treated with a calcineurin inhibitor-based immunosuppression by immunohistology using a FITC-labelled anti-TIRC7 mAb following the biopsy-confirmed diagnosis of acute rejections. Joint tissues isolated from patients with Rheumatoid Arthritis (RA) were subjected to immunohistology using a directly FITC labelled anti-TIRC7 mAb. Flow cytometric analysis was performed using an anti-TIRC7 mAb on PBL activated with alloantigen. TIRC7 protein expression was determined on CD4+ and CD8+ T cells using a polyclonal TIRC7-specific antibody. Cells were stained with conjugated mAb (CD28, CD45RO) and the samples were analyzed by a FACScalibur flow cytometer.

Immune fluorescent microscopy revealed that lymphocytes of human tissues obtained from patients with acute rejection under immunosuppressive combination therapy with various agents (Calcineurin inhibitors; FK 506/Cylosporin A (CyA), methyl prednisolone (MP), and mycophenolate mofetil (CC) strongly expressed TIRC7 (n=5) whereas normal kidneys did not show any TIRC7 expression. TIRC7 mAb staining revealed strong upregulation of TIRC7 protein expression in tissues obtained from knee joint samples as well as in mononuclear cells from joint fluid obtained from patients with established RA. No staining was observed in all experiments using control antibody for staining. On human PBL TIRC7 was predominantly induced within the first hour of activation on CD4+45RO+28+ and CD8+45RO+28+ but less on CD28-negative T cells suggesting primary expression on resting memory T cells but less on naïve and effector/memory T cells.

These experiments demonstrate that TIRC7 is strongly upregulated following in vitro activation of resting memory T cells but less on naïve (CD45RO−) and effector/memory (CD28−) T cells and also in vivo in patients with Rheumatoid Arthritis (RA) and in rejected kidney tissues. In summary, these studies suggest TIRC7 might be suitable for targeting of memory T cells and as a diagnostic marker of immune activation.

Example 2

Detection of TIRC7 in a bodily fluid for diagnosing transplant rejection This experiment was performed in order to investigate whether expression of TIRC7 can be detected in a bodily fluid and, if so, whether the detected level of TIRC7 expression is indicative of the status of the immune response. In particular, the aim of this study was to analyze the functional role of TIRC7 as early biomarker to detect rejection in order to be able to replace biopsy interventions with a simple diagnostic for monitoring after transplantation. Therefore, the expression of the TIRC7 protein was surveyed using specific monoclonal antibodies (mAbs) during rejection of human kidney allografts after transplantation in urine of patients after kidney transplantation.

Kidney biopsy specimens (n=5) were obtained from the patients undergoing histologically confirmed acute rejection. Joint tissues and fluid mononuclear cells were obtained from the patients diagnosed of established RA. These tissues were immunohistologically stained with an FITC labeled mAb against TIRC7. Peripheral blood lymphocytes were obtained from healthy volunteers. The cells were cultured with mitogens. And subsequently stained with conjugated mAbs (CD4, CD8, CD 16, CD 19, CD28, CD45R0, and anti-TIRC7 mAb) and analyzed by a FACScalibur flow cytometer.

For mRNA expression analysis urine was centrifuged at 10.000 rpm and 4° C. for 15 minutes. Pellet was washed in 1 mL phosphate-buffered saline and centrifuged at 14.000 rpm for 7 minutes at 4° C. Supernatants were discarded and total RNA was isolated from the pellet using the RNeasy™ Kit (Qiagen, Hilden, Germany). CDNA synthesis and real-time RT-PCR were performed as recently described by Kotsch et al., Transplantation 77 (2004), 1866-1875. Briefly, mRNA measurement for IP-IO was performed using the ABI PRISM™-7700DS System (Applied Biosystems) with 40 cycles of 15 seconds denaturation at 95° C. and a 60 seconds annealing-extension step at 6O° C. Gene expression of histone mRNA was used for normalization given by the formula $2^{-\Delta t}$. All primers and probes were designed using Primer Express software (Applied Biosystems) and validated at the Institute of Medical Immunology, Universitatsmedizin Charite, Berlin. A total of 120 urine specimens were analyzed post Tx for the individual kinetic IP-10 mRNA expression for 17 patients with aRx episodes. The $2^{-\Delta t}$ values of the rejection patients were set in relation to the arithmetic mean of the mRNA IP-10 expression values from the reference group based upon 85 urinary samples derived from 26 patients with stable renal function ($2^{-\Delta\Delta Ct}$ method); see Kotsch et al. (2004), supra. The normalized data from the control patients were further used to establish 2s-confidence intervals.

Figure 1:
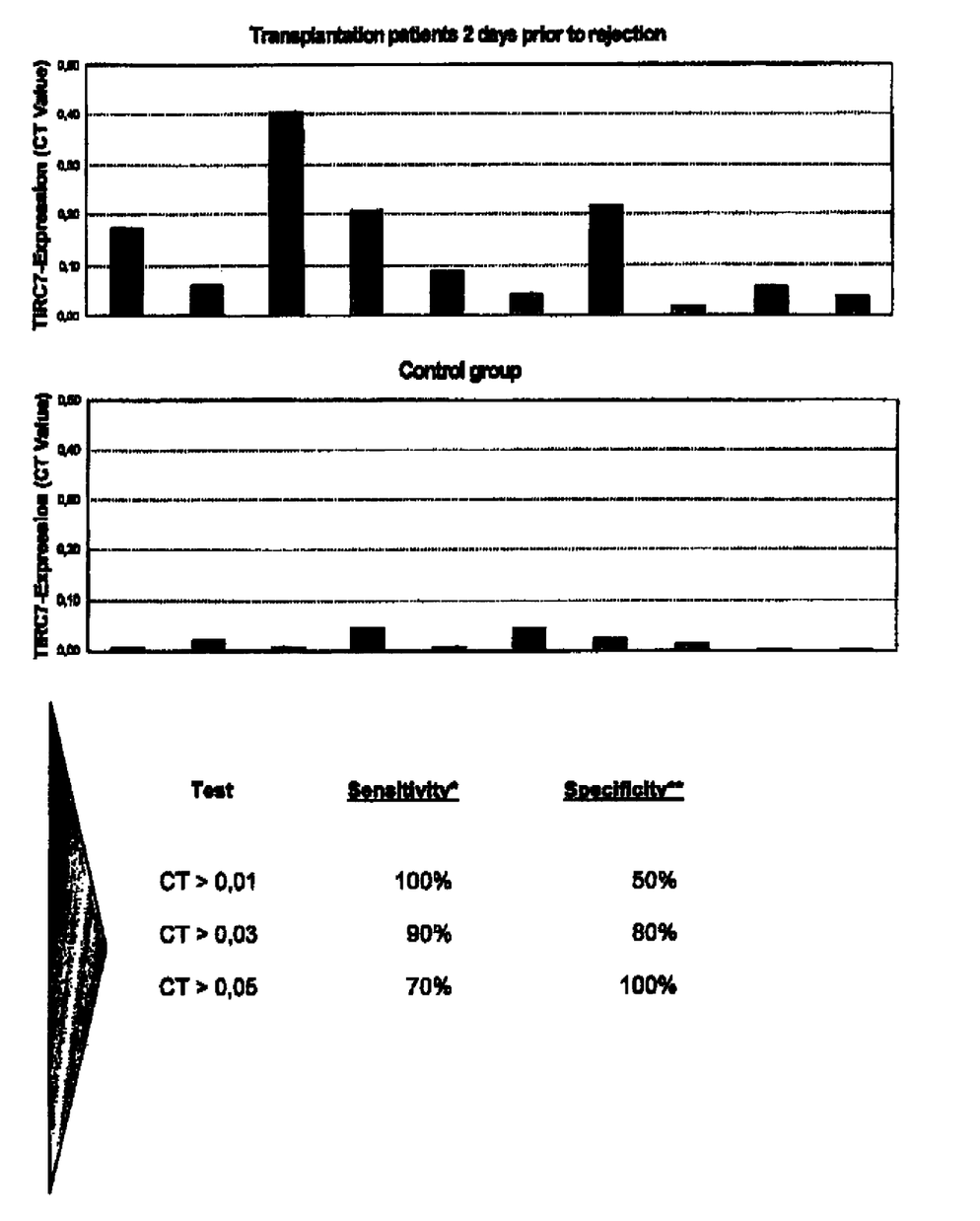

As shown in FIG. 1 TIRC7 is induced in cDNA isolated from urine of patients with kidney transplantation 2 days prior to rejection. These results suggest that TIRC7 can serve as early biomarker to detect rejection in urine and thus establishes for the first time TIRC7 as a useful non-invasive diagnostic marker to detect early of immune activation.

What is claimed is:

1. A non-invasive method of detecting an early and/or undesired immune response evoked by a disorder or disease associated with autoimmunity in a subject, said method comprising
   a) obtaining a sample from the subject, which sample is a bodily fluid;
   b) analyzing expression of T-cell immune response cDNA 7 (TIRC7) in the sample;
   c) comparing the expression of TIRC7 in the sample with the expression of TIRC7 in a control sample from a subject who does not have early and/or undesired immune response evoked by the disorder or disease; and
   d) determining that the subject has early and/or undesired immune response evoked by the disorder or disease if an up-regulation of TIRC7 is found in the sample.

2. The method of claim 1, wherein the disorder or disease is psoriasis, multiple sclerosis, arthritis, or transplant rejection.

3. The method of claim 1, wherein the disorder or disease is kidney transplant rejection or rheumatoid arthritis.

4. The method of claim 1, wherein in step b), the expression of TIRC7 is determined by transcriptional activity of the TIRC7 gene or the amount of TIRC7 protein.

5. The method of claim 1, wherein in step b), the expression of TIRC7 is analyzed by analyzing expression of a polynucleotide for the TIRC7.

6. The method of claim 5, wherein the expression of TIRC7 is analyzed by analyzing RNA levels of TIRC7.

7. The method of claim 5, wherein the expression of TIRC7 is analyzed by applying the nucleic acids to a bioarray.

8. The method of claim 5, wherein the expression of TIRC7 is mRNA and the mRNA is amplified using real-time reverse transcriptase polymerase chain reaction (qRT-PCR).

9. The method of claim 4, wherein the expression of TIRC7 is determined by transcriptional activity of the TIRC7 gene or the amount of TIRC7 protein.

10. The method of claim 1, wherein the bodily fluid is urine.

* * * * *

UNITED STATES PATENT AND TRADEMARK OFFICE
CERTIFICATE OF CORRECTION

| | | |
|---|---|---|
| PATENT NO. | : 8,642,512 B2 | Page 1 of 1 |
| APPLICATION NO. | : 11/914617 | |
| DATED | : February 4, 2014 | |
| INVENTOR(S) | : Utku | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1533 days.

Signed and Sealed this
Seventh Day of July, 2015

Michelle K. Lee
*Director of the United States Patent and Trademark Office*